(12) United States Patent
Lin et al.

(10) Patent No.: US 7,646,487 B2
(45) Date of Patent: Jan. 12, 2010

(54) REFLECTANCE MEASURING APPARATUS

(75) Inventors: Kun-Wei Lin, Tainan County (TW); Yi-Hsuan Chiang, Pingtung County (TW); Lung-Yu Cheng, Tainan (TW); Yu-Hsiu Chang, Changhua County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 0 days.

(21) Appl. No.: 12/081,179

(22) Filed: Apr. 11, 2008

(65) Prior Publication Data

US 2009/0128823 A1 May 21, 2009

(30) Foreign Application Priority Data

Nov. 20, 2007 (TW) .............................. 96143833 A

(51) Int. Cl.
*G01N 21/55* (2006.01)
(52) U.S. Cl. .................................... 356/445; 356/237.1
(58) Field of Classification Search ......... 356/445–447, 356/36, 237.1–237.6
See application file for complete search history.

(56) References Cited

U.S. PATENT DOCUMENTS

| 5,406,367 | A | | 4/1995 | Sopori |
| 5,883,714 | A | * | 3/1999 | Jann et al. .................... 356/484 |
| 7,119,897 | B2 | * | 10/2006 | Vaez-Iravani et al. ..... 356/237.4 |
| 2002/0041374 | A1 | * | 4/2002 | Ohshima et al. .......... 356/237.2 |
| 2005/0002021 | A1 | * | 1/2005 | Kreh et al. ............... 356/237.2 |

\* cited by examiner

*Primary Examiner*—Gregory J Toatley, Jr.
*Assistant Examiner*—Tri T Ton
(74) *Attorney, Agent, or Firm*—Birch, Stewart, Kolasch & Birch, LLP

(57) ABSTRACT

A reflectance measuring apparatus is provided in the present invention. In addition to measuring the intensity of light directly reflected from a sample, the apparatus is further capable of collecting large-angle reflected light scattered from the sample through a reflecting cover disposed over the sample and measuring the intensity thereof. In one embodiment, the reflecting cover has a parabolic surface for modulating the large-angle reflected light to become parallel light projecting onto a photo-detector. In another embodiment, the reflecting cover has an elliptic surface for modulating the large-angle scattered light to focus on the photo-detector.

16 Claims, 10 Drawing Sheets

REFLECTANCE MEASURING APPARATUS

BACKGROUND OF THE INVENTION

1. Field of the Invention

The present invention generally relates to an optical detection apparatus and, more particularly, to a reflectance measuring apparatus capable of measuring the reflectance of large-angle reflected light scattered from a sample.

2. Description of the Prior Art

The problems due to global warming have attracted tremendous attention. It is reported that the fossil fuels will be used up in less than 60 years, which leads to raised cost of fossil fuels related products. Therefore, the development in renewable energies has been a key topic of research. The solar energy, being natural and free of pollutions, has become the most commercially competitive one among the renewable energies.

Generally, the solar cell uses an anti-reflecting layer formed thereon to prevent the incident solar beams from being reflected. Since the surface of a silicon wafer is mirror-like and reflects over 30% of the incident solar beams, 30% of the solar energy is lost without the anti-reflecting layer. In addition to the anti-reflecting layer, the surface of a single-crystal silicon solar cell is further textured to reduce reflection of the incident solar beams. The textured surface has a plurality of pyramids, which enable the incident solar beams to experience at least two reflections before escaping from the surface. This decreases the percentage of the incident solar beams being reflected.

In order to measure the reflectance of a localized surface of a solar cell to evaluate the manufacturing quality, U.S. Pat. No. 5,406,367 discloses an apparatus and a method, wherein a light integrating sphere is disposed on a sample to collect large-angle reflected light to be detected by a photo-detector for intensity measurement. However, in this disclosure, the spreading angle is restricted while measuring the spreading angle of the reflected light because the reflected light cannot entirely enter the light integrating sphere if the spreading angle of the reflected light is too large, which leads to measuring error. Even by enlarging the aperture on the light integrating sphere so that the large-angle reflected light can enter the light integrating sphere, measuring error becomes larger because the reflected light inside the light integrating sphere escapes easily through the enlarged aperture.

SUMMARY OF THE INVENTION

It is an object of the present invention to provide a reflectance measuring apparatus using a reflecting cover capable of modulating large-angle reflected light scattered from a sample to a photo-detector so as to measure the reflectance with a simplified structure to improve measurement precision and reduce the cost.

In one embodiment, the present invention provides a reflectance measuring apparatus, comprising: a light source, capable of providing detection light; a first light detection portion, capable of detecting the intensity of light; a light source modulating portion, capable of modulating the detection light to a sample and modulating reflected light from the sample to the first light detection portion; a second light detection portion, capable of detecting the intensity of light; and a reflecting cover, being disposed between the sample and the light source modulating portion, the reflecting cover comprising a parabolic surface with a focal point located at the sample so that the parabolic surface is capable of modulating the reflected light to become parallel light to the second light detection portion.

In another embodiment, the present invention provides a reflectance measuring apparatus, comprising: a light source, capable of providing detection light; a first light detection portion, capable of detecting the intensity of light; a light source modulating portion, capable of modulating the detection light to a sample and modulating reflected light from the sample to the first light detection portion; a second light detection portion, capable of detecting the intensity of light; and a reflecting cover, being disposed between the sample and the light source modulating portion, the reflecting cover comprising an elliptic surface with a first focal point located at the sample so that the elliptic surface is capable of modulating the reflected light scattered from the sample to focus on the second light detection portion which is disposed at a second focal point of the elliptic surface.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PREFERRED EMBODIMENT

The present invention can be exemplified by but not limited to the preferred embodiments as described hereinafter.

Figure 1A:
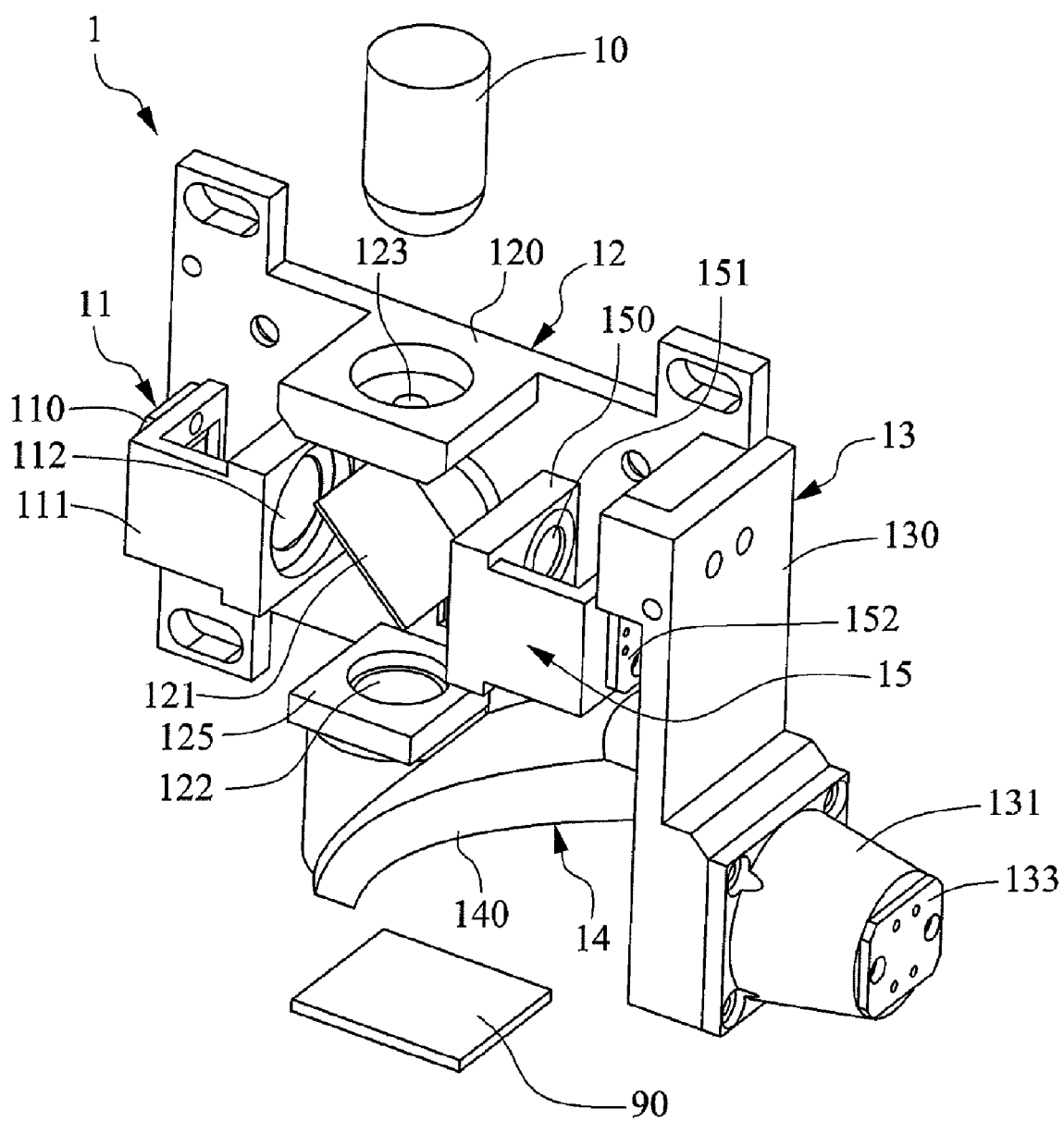
FIG. 1A and FIG. 1B show 3-D schematic views of a reflectance measuring apparatus and unassembled parts thereof according to a first embodiment of the present invention.
Figure 1B:
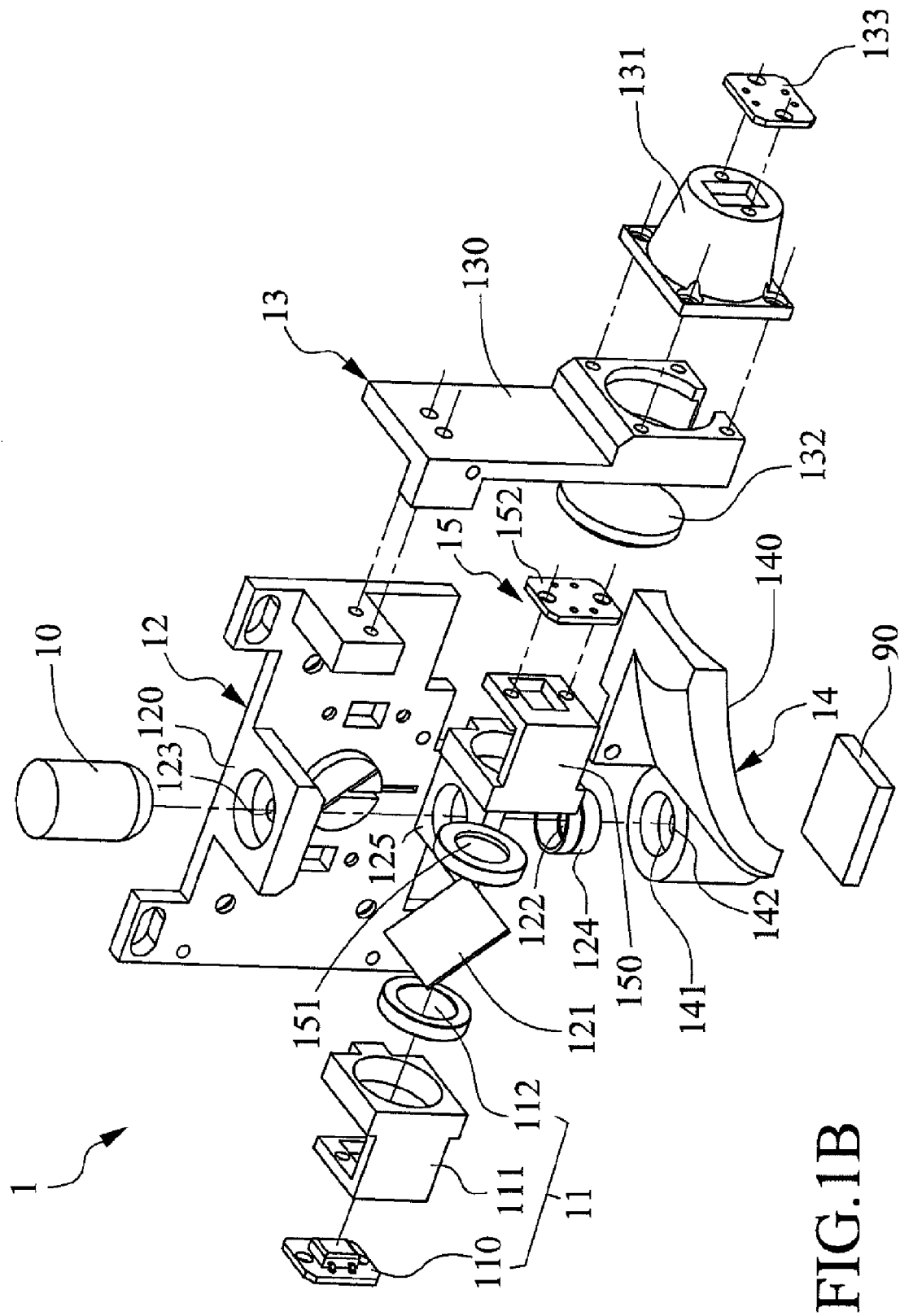

Please refer to FIG. 1A and FIG. 1B, which show 3-D schematic views of a reflectance measuring apparatus and unassembled parts thereof according to a first embodiment of the present invention. The reflectance measuring apparatus comprises a light source 10, a first light detection portion 11, a light source modulating portion 12, a second light detection portion 13 and a reflecting cover 14. The light source 10 is a collimated light source or a general light source capable of generating detection light. In the present embodiment, the light source 10 is a collimated light source. The collimated light source is a laser light source but not limited thereto.

Figure 2:
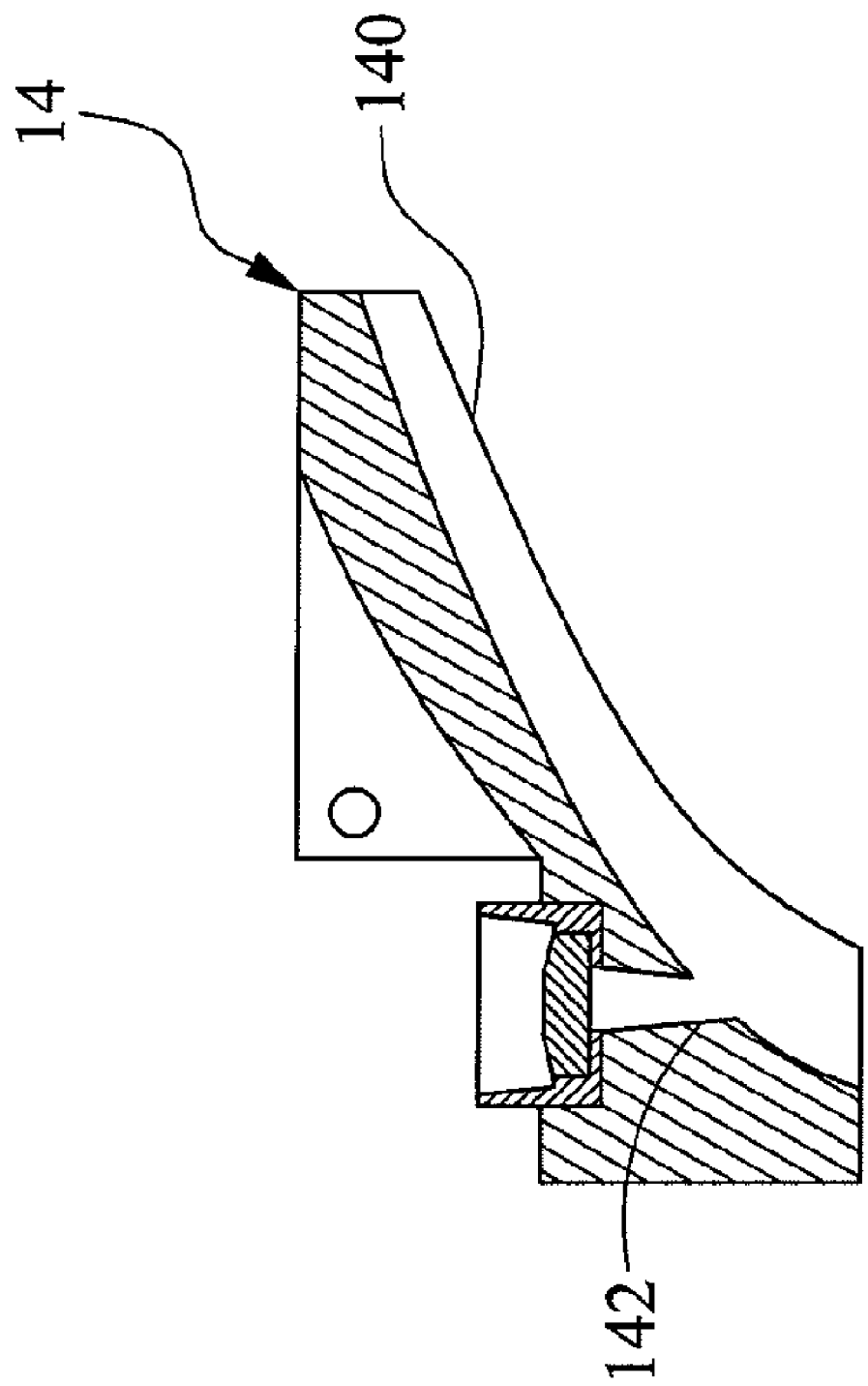
FIG. 2 shows a cross-sectional view of a reflecting cover according to the present invention.

The light source modulating portion 12 is disposed on one side of the light source 10 to receive the detection light. The light source modulating portion 12 is capable of modulating the detection light to a sample 90. In the present embodiment, the light source modulating portion 12 further comprises a base 120, a beam splitter 121 and a lens 122. On one side of the base 120, an aperture 123 is disposed to allow the detection light to pass through. The beam splitter 121 is disposed corresponding to the aperture 123. The beam splitter 121 is capable of splitting the detection light into a first detection light and a second detection light. The lens 122 is fixedly disposed in a ring 124. The ring 124 is further fixedly disposed in a socket 141 of the reflecting cover 14. During assembly, the lens 122 is aligned with a protrusion base 125 so that the lens 122 and the beam splitter 121 are capable of focusing and projecting the first detection light to the sample 90. Because the focal point of the lens 122 has to be overlapped with the focal point of the parabolic reflecting cover 14 that is difficult to achieve, therefore the focal point of the lens 122 and the focal point of the reflecting cover 14 are adjusted to overlap first, and then are further aligned with the aperture in the protrusion base 125. The first light detection portion 11 is disposed on one side of the light source modulating portion 12 to detect light intensity. In the present embodiment, the first light detection portion 11 further comprises a fixing part 111, a lens 112 and a photo-detector 110. The lens 112 is disposed between the beam splitter 121 and the photo-detector 110. Certainly, in another embodiment, if the photo-detector 110 is capable of receiving a large range of light, the lens 112 is not necessary and can be removed. The reflecting cover 14 is disposed between the sample 90 and the light source modulating portion 12. The reflecting cover 14 is capable of introducing reflected light scattered from the sample 90 to the second light detection portion 13. The reflecting cover 14 comprises a reflecting surface 140. In the present embodiment, the reflecting surface 140 is a parabolic surface. Moreover, to improver reflection, the reflecting surface 140 is further coated with a reflecting film. The material used to form the reflecting film is well known those in the art and is thus not repeated here. Moreover, on the reflecting cover 14 is disposed a socket 141 corresponding to the protrusion base 125. The socket 141 is capable of fixing the ring 124. As shown in FIG. 2, the reflecting cover 14 comprises an aperture 142 formed in the socket 141 for the detection light and the reflected light to pass through. In one embodiment, the aperture 142 is cone-shaped.

Referring to FIG. 1A and FIG. 1B, the second light detection portion 13 is disposed on one side of the reflecting cover 14 so as to detect the intensity of light reflected from the reflecting cover 14. The second light detection portion 13 further comprises a fixing part 130, a cover 131, a lens 132 and a photo-detector 133. The lens 132 is fixed on the fixing part 130 and is disposed between the reflecting cover 14 and the photo-detector 133. The cover 131 is connected to the fixing part 130 so as to cover one side of the lens 132. The photo-detector 133 is disposed on one side of the cover 131. Certainly, in another embodiment, if the photo-detector 133 is capable of receiving a large range of light, the lens 132 is not necessary and can be removed. On another side of the beam splitter 121 is further disposed a light monitoring portion 15, comprising a fixing part 150, a photo-detector 152 and a lens 151. The lens 151, provided on the fixing part 150, is disposed between the beam splitter 121 and the photo-detector 152. The lens 151 is capable of focusing the second detection light on the photo-detector 152. The light monitoring portion 15 is capable of monitoring and controlling the intensity of the detection light from the light source 10.

Figure 3:
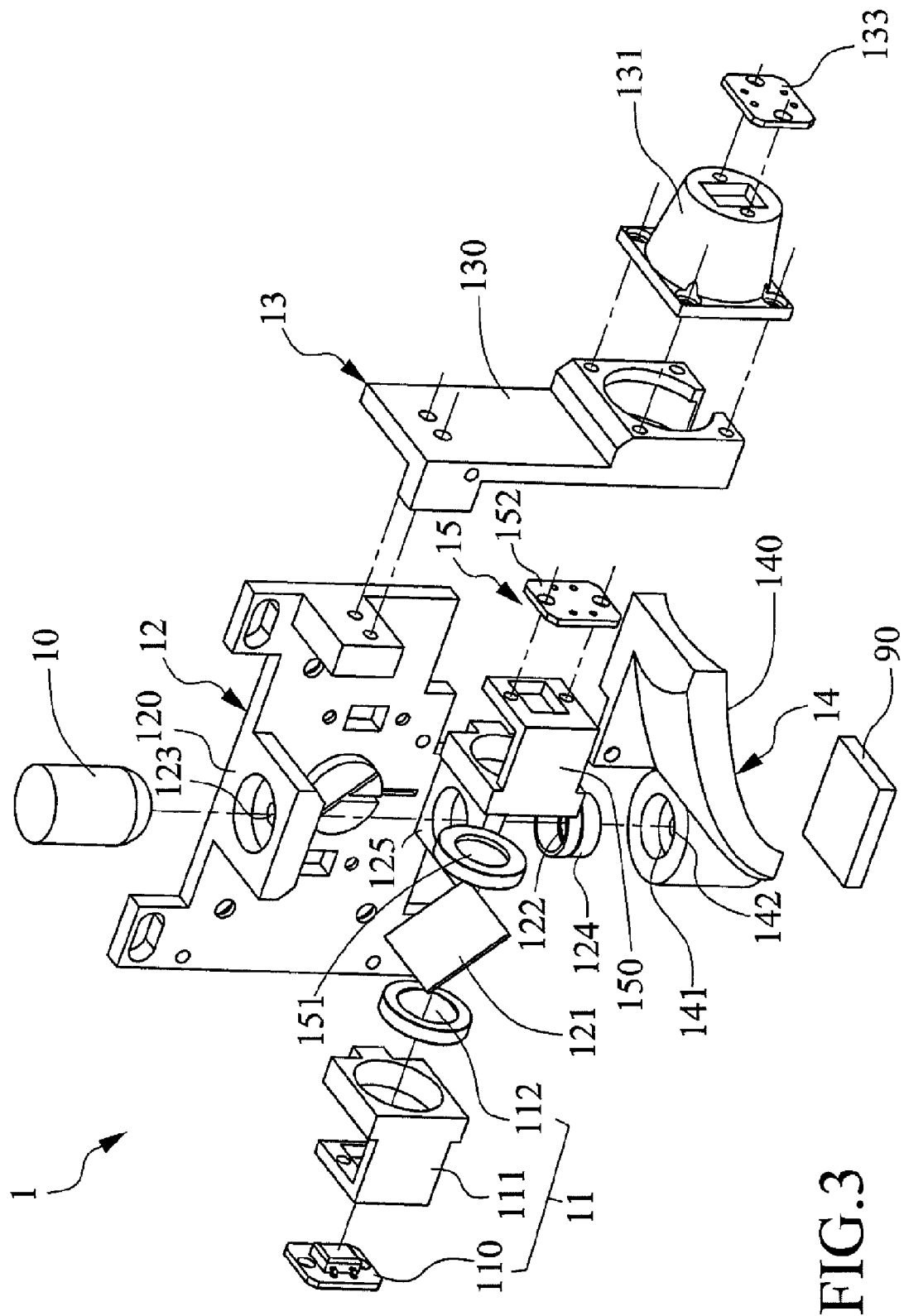
FIG. 3 shows a 3-D schematic view of unassembled parts of a reflectance measuring apparatus according to a second embodiment of the present invention.

Please refer to FIG. 3, which shows a 3-D schematic view of unassembled parts of a reflectance measuring apparatus according to a second embodiment of the present invention. In the present embodiment, most of the elements are similar to those in FIG. 1B except that the reflecting surface of the reflecting cover is an elliptic surface. The first focal point of the elliptic surface is designed to be located on the sample. Therefore, the large-angle reflected light scattered at the first focal point will be focused on the second focal point by the elliptic surface focus. The second light detection portion is disposed at the second focal point. Therefore, in the present embodiment, a lens is not required in the second light detection portion 13 to focus the reflected light on the photo-detector 133.

Figure 4A:
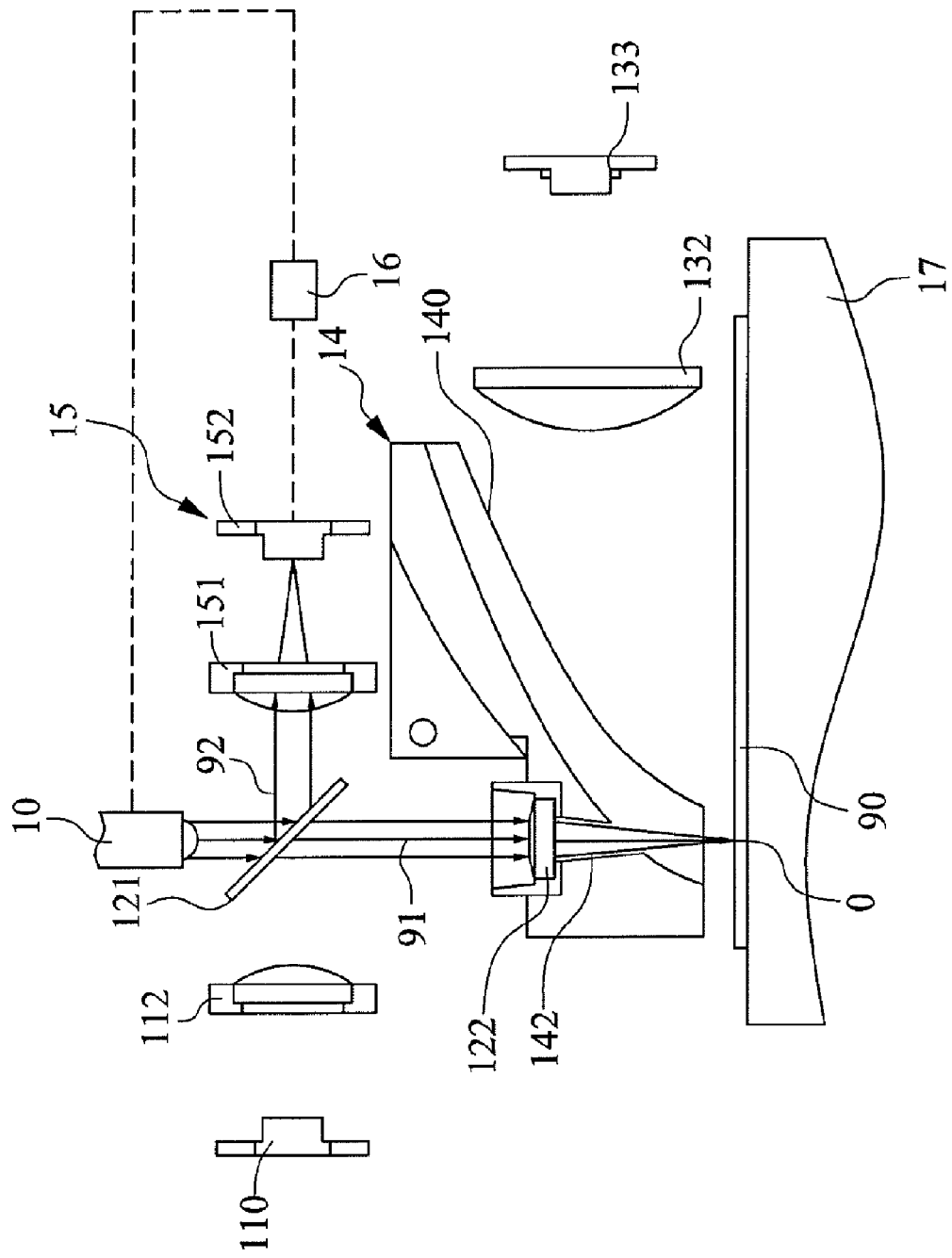
FIG. 4A and FIG. 4B show cross-sectional views of a reflecting cover comprising a parabolic surface with optical paths according to the present invention.
Figure 4B:
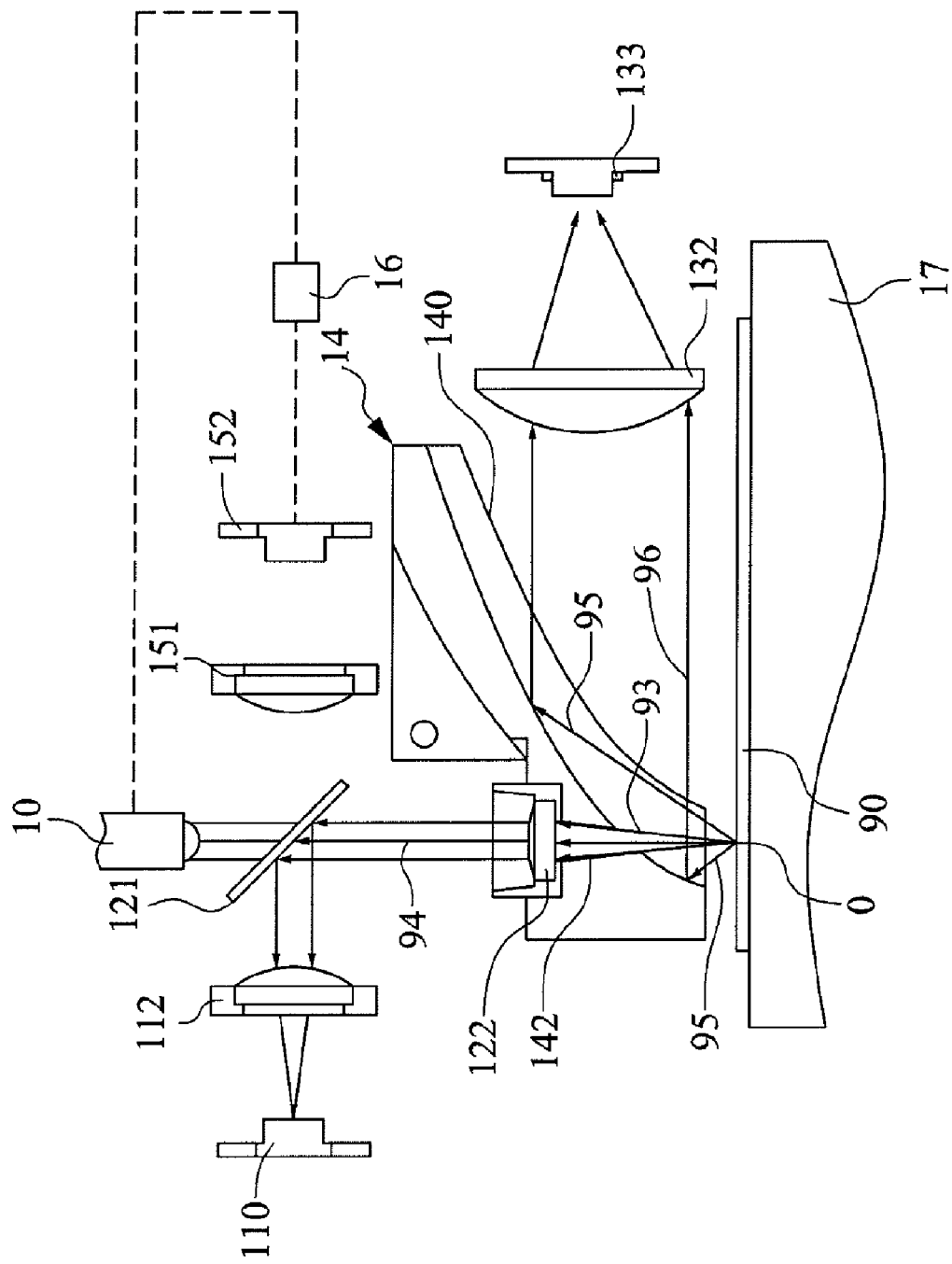

Please refer to FIG. 1A, FIG. 4A and FIG. 4B, wherein FIG. 4A and FIG. 4B show cross-sectional views of a reflecting cover comprising a parabolic surface with optical paths according to the present invention. In the present embodiment, the reflecting surface 140 of the reflecting cover 14 is a parabolic surface. Collimated laser light from the light source 10 is incident on the beam splitter 121 through an aperture 123 in the base 120. The beam splitter 121 splits the laser light into a first detection light 91 and a second detection light 92. The first detection light 91 passes through the beam splitter 121, and the second detection light 92 is reflected by the beam splitter 121 to the light monitoring portion 15. The second detection light 92 is focused on the photo-detector 152 through the lens 151. After the intensity is detected by the photo-detector 152, the laser controller 16 receives a detection signal from the photo-detector 152 so as to stabilize the input power. On the other hand, the first detection light 91 passing through the beam splitter 121 enters the lens 122 to focus at O on the sample 90 through the aperture 142. In the present embodiment, the sample 90 is disposed on a carrier 17 capable of performing three-axis movement.

In FIG. 4B, the reflected light from the sample 90 is split into two parts, one of which is reflected light 93 back to the lens 122 in the original optical paths through the aperture 142. In the present embodiment, the aperture 142 is cone-shaped so that the aperture 142 is capable of restricting the spreading angle of reflected light 93 to the lens 122 to insure that the lens 122 collimates the reflected light 93 to become parallel light 94. The collimated parallel light 94 enters the lens 112 and focuses on photo-detector 110 through the beam splitter 121. Thereby, the intensity $I_1$ of the reflected light 93 is measured. Another part of the reflected light is large-angle reflected light 95 reflected by the reflecting cover 14. The reflecting surface 140 of the reflecting cover 14 is coated with a high-reflectance film capable of reflecting laser light. Since the reflecting surface 140 of the reflecting cover 14 is half of a parabolic surface with a focal point designed to be disposed on the sample (O in the figure), the reflected light 95 scattered at O is collimated by the reflecting surface 140 to become parallel light 96. The parallel light 96 is further focuses on the photo-detector 133 through the lens 132. Thereby, the intensity $I_2$ of the reflected light 93 is measured. $I_2$ and $I_1$ can be summed to obtain the total intensity of the reflected light. Then, a carrier 17 is used to change the detection position of the sample 90 so as to scan the entire sample 90 for reflectance measurement.

Figure 5:
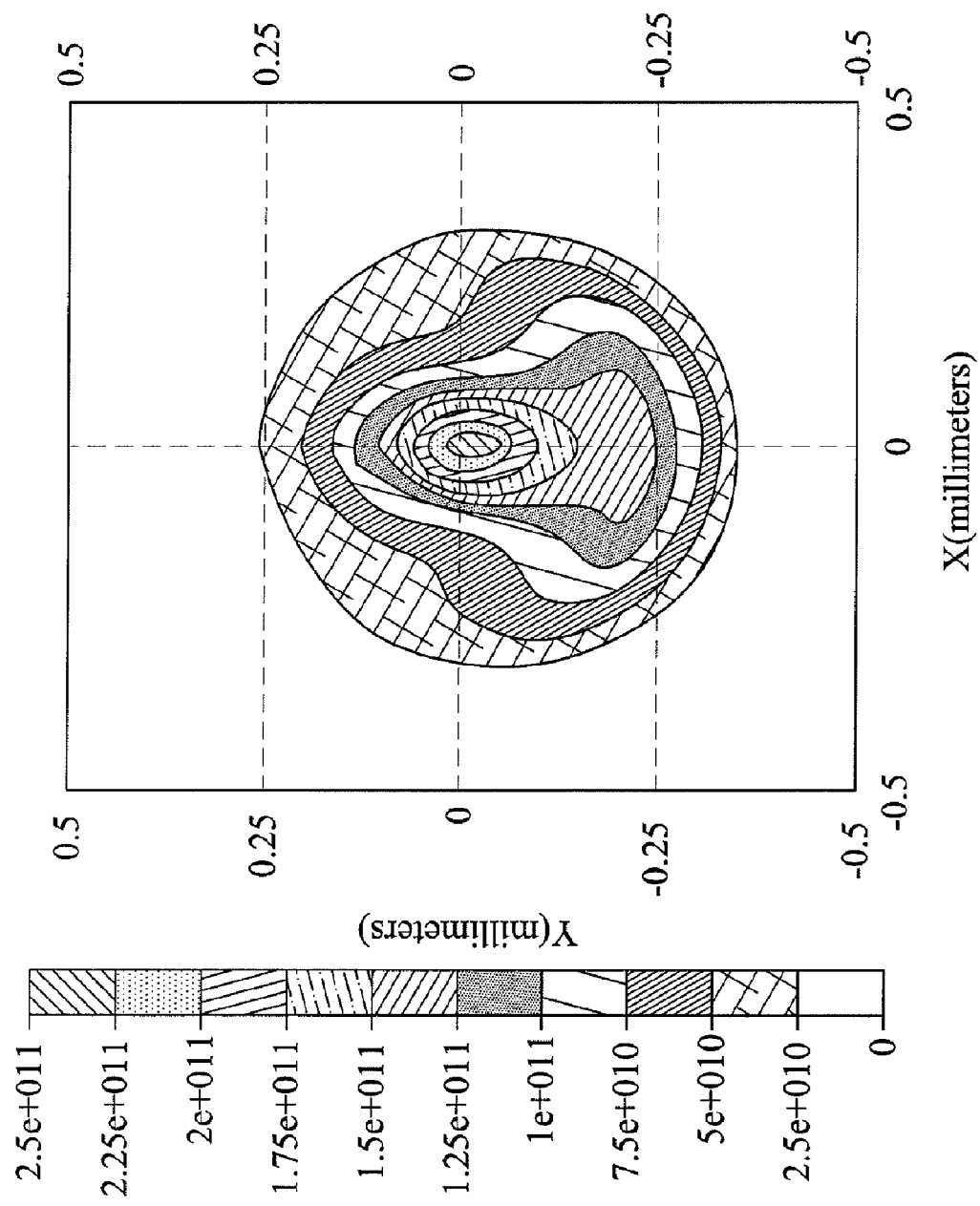
FIG. 5 is a simulation result of a light spot detected by the first light detection portion.
Figure 6:
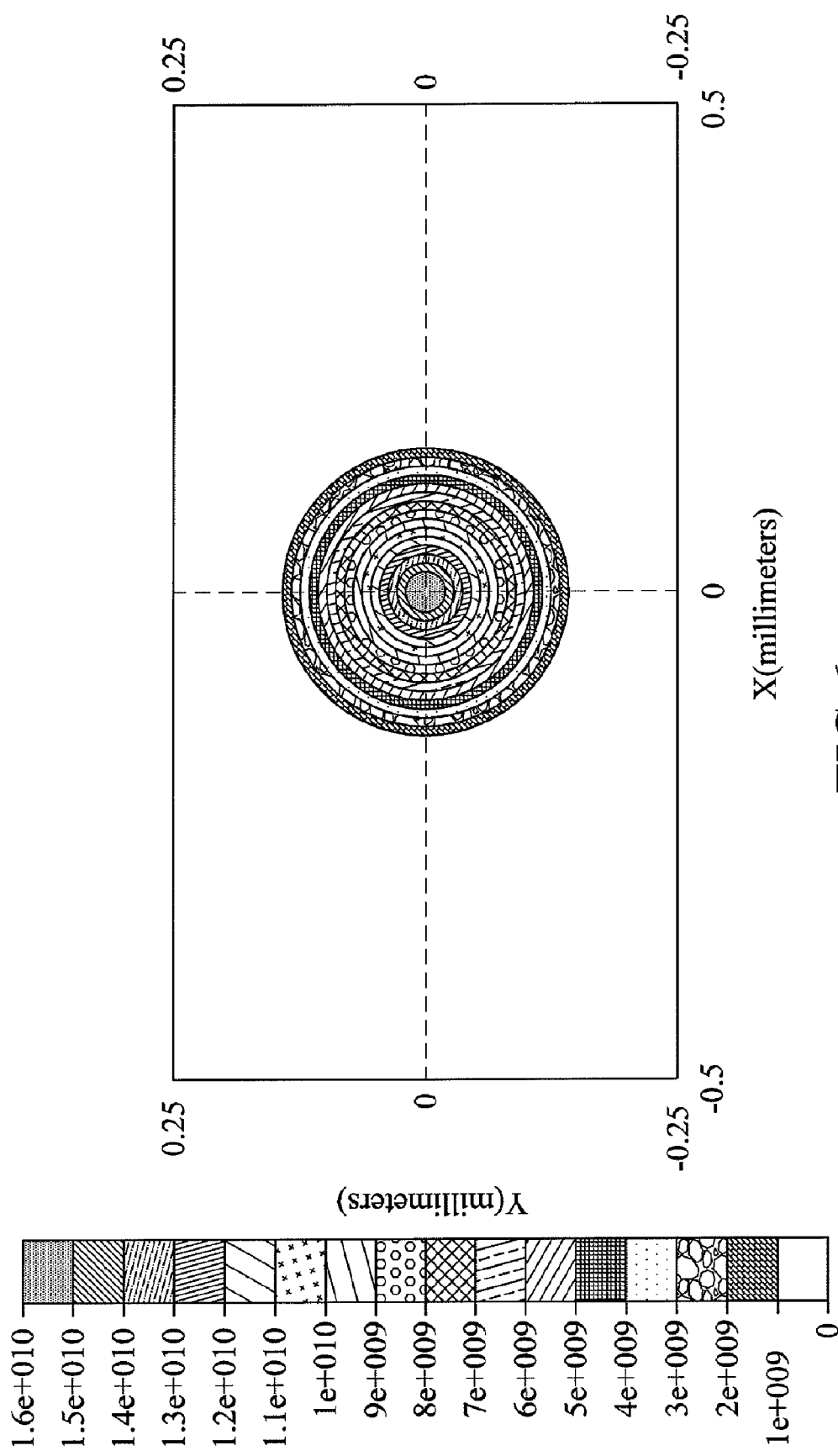
FIG. 6 is a simulation result of a light spot detected by the second light detection portion.

FIG. 5 and FIG. 6 are simulation results of a light spot detected by the first light detection portion and the second light detection portion, respectively. Taking a reflecting cover having a parabolic surface simulated by optical simulation software at a spreading angle of 90 degrees for example, part of the reflected light is focused on the photo-detector 110 through the lens 112, the light spot being shown in FIG. 5. The reflected light with a larger spreading angle is collimated to become parallel light and is focused on the photo-detector 133 through the lens 132, the light spot being shown in FIG. 6. It is possible to measure the reflected light intensity if the measuring area of the photo-detector is larger than the light spot. Therefore, the reflected light with a large spreading angle can be measured and the reflecting cover is simplified with lowered cost.

Figure 7A:
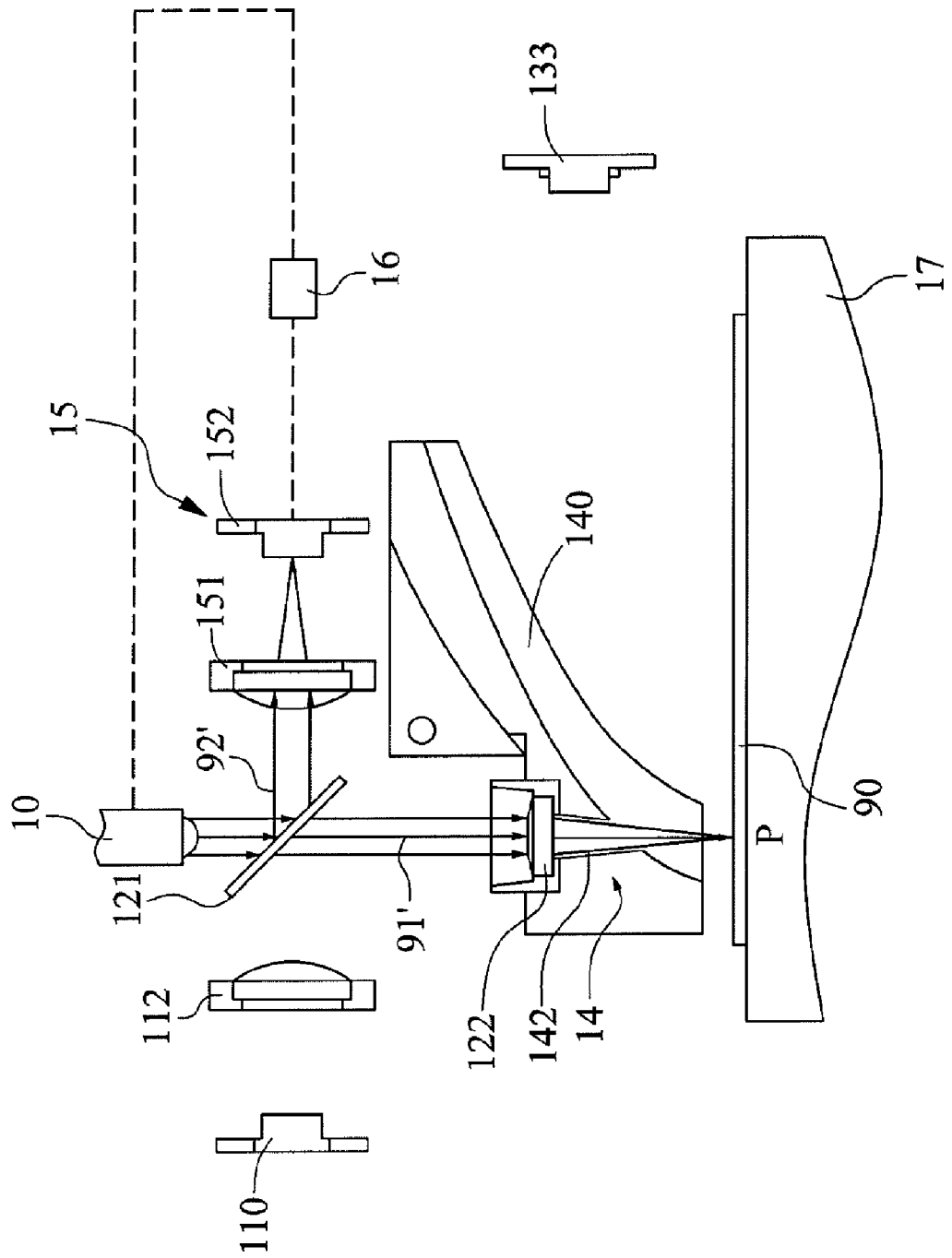
FIG. 7A and FIG. 7B show cross-sectional views of a reflecting cover comprising an elliptic surface with optical paths according to the present invention.

Please refer to FIG. 1B and FIG. 7A, wherein FIG. 7A shows cross-sectional view of a reflecting cover comprising an elliptic surface with an optical path according to the present invention. In the present embodiment, the reflecting surface 140 of the reflecting cover 14 is an elliptic surface. When the collimated laser light from the light source 10 passes through the aperture 123 of the base 120 into the beam splitter 121, the laser light is split into a first detection light 91' and a second detection light 92' by the beam splitter 121. The first detection light 91' passes through the beam splitter 121, and the second detection light 92' is reflected to the light monitoring portion 15 by the beam splitter 121. The second detection light 92' is focused on photo-detector 152 through the lens 151'. After the intensity is detected by the photo-detector 152, the laser controller 16 receives a detection signal from the photo-detector 152 so as to stabilize the input power. On the other hand, the first detection light 91' passing through the beam splitter 121 enters the lens 122 to focus at P on the sample 90 through the aperture 142. In the present embodiment, the sample 90 is disposed on a carrier 17 capable of performing three-axis movement.

Figure 7B:
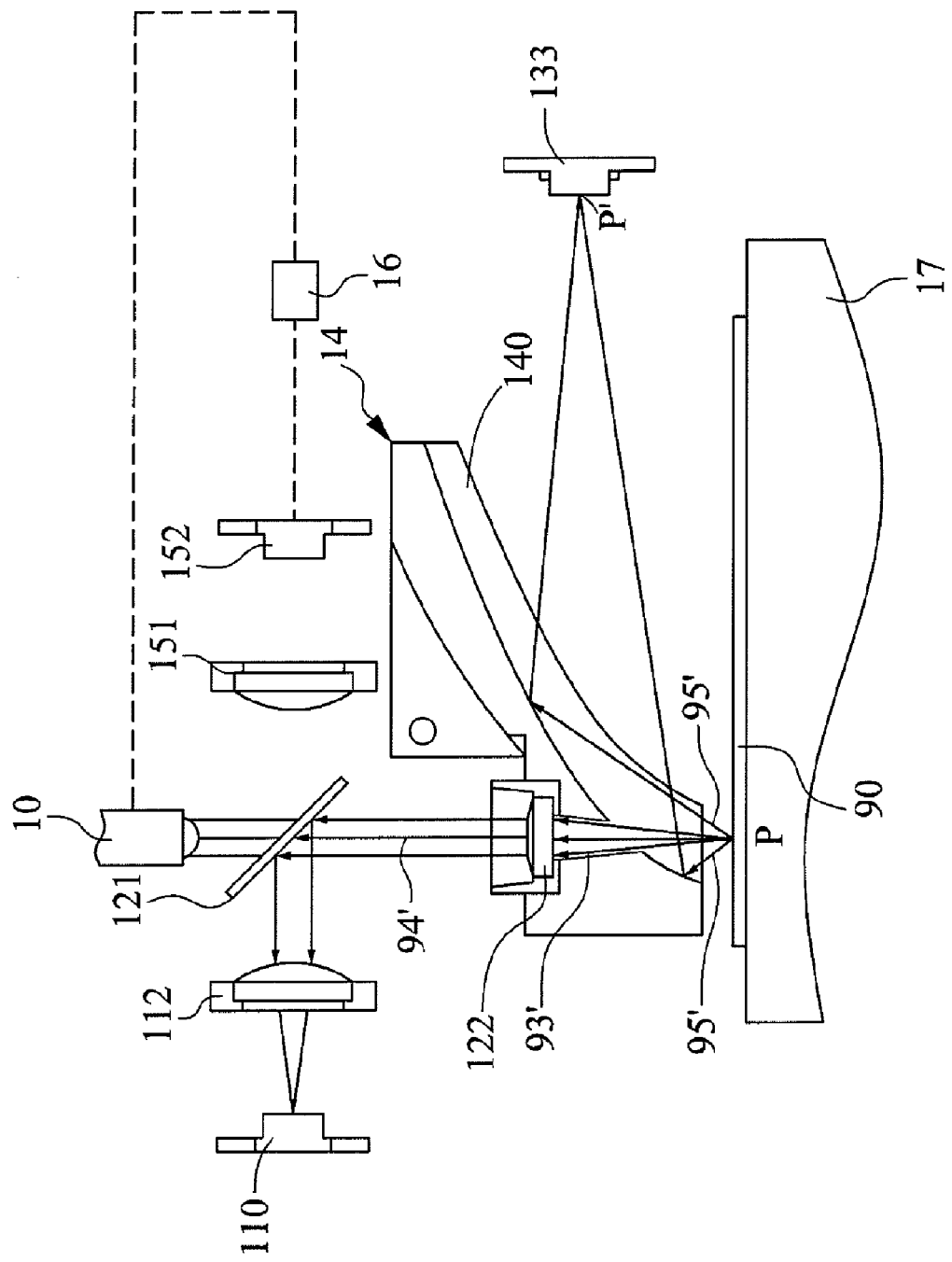

In FIG. 7B, the reflected light from the sample 90 is split into two parts, one of which is reflected light 93' back to the lens 122 in the original optical paths through the aperture 142. In the present embodiment, the aperture 142 is cone-shaped so that the aperture 142 is capable of restricting the spreading angle of reflected light 93' to the lens 122 to insure that the lens 122 collimates the reflected light 93' to become parallel light 94'. The collimated parallel light 94' enters the lens 112 and focuses on photo-detector 110 through the beam splitter 121. Thereby, the intensity $I_1'$ of the reflected light 93' is measured. Another part of the reflected light is large-angle reflected light 95' reflected by the reflecting cover 14. The reflecting surface 140 of the reflecting cover 14 is coated with a high-reflectance film capable of reflecting laser light. Since the reflecting surface 140 of the reflecting cover 14 is an elliptic surface with a first focal point designed to be disposed at P on the sample, the large-angle reflected light 95' scattered at P is focused at a second focal point P' by the elliptic surface. The photo-detector 133 is disposed at P' and is capable of detecting the reflected light intensity $I_2'$. $I_2'$ and $I_1'$ can be summed to obtain the total intensity of the reflected light. Then, a carrier 17 is used to change the detection position of the sample 90 so as to scan the entire sample 90 for reflectance measurement.

According to the above discussion, it is apparent that the present invention discloses a reflectance measuring apparatus capable of achieving higher measuring precision and reducing the cost using a simplified structure. Therefore, the present invention is novel, useful and non-obvious.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A reflectance measuring apparatus, comprising:
   a light source, capable of providing detection light;
   a first light detection portion, capable of detecting the intensity of light;
   a light source modulating portion capable of modulating the detection light to a sample and modulating reflected light from the sample to the first light detection portion, the light source modulating portion comprising: a beam splitter capable of splitting the detection light into a first detection light and a second detection light; and a lens capable of focusing the first detection light on the sample;
   a second light detection portion, capable of detecting the intensity of light; and
   a reflecting cover comprising: a cone-shaped aperture formed therein for the detection light and the reflected light to pass through; and a parabolic surface with a focal point located at the sample so that the parabolic surface is capable of modulating the reflected light to become parallel light to the second light detection portion, the reflecting cover being disposed between the sample and the light source modulating portion, the reflecting cover being capable of introducing the reflected light scattered from the sample to the second light detection portion.

2. The reflectance measuring apparatus as recited in claim 1, wherein the parabolic surface is coated with a reflecting film formed thereon.

3. The reflectance measuring apparatus as recited in claim 1, wherein a lens is disposed between the first light detection portion and the light source modulating portion.

4. The reflectance measuring apparatus as recited in claim 1, further comprising a light monitoring portion capable of receiving the second detection light so as to monitor the power intensity of the second detection light.

5. The reflectance measuring apparatus as recited in claim 4, where the light monitoring portion further comprises:
   a photo-detector; and
   a lens, being disposed between the beam splitter and the photo-detector so that the lens is capable of focusing the second detection light on the photo-detector.

6. The reflectance measuring apparatus as recited in claim 1, wherein a lens is disposed between the first light detection portion and the light source modulating portion.

7. The reflectance measuring apparatus as recited in claim 1, wherein the light source is capable of providing a collimated light source.

8. The reflectance measuring apparatus as recited in claim 7, wherein the collimated light source is a laser.

9. A reflectance measuring apparatus, comprising:
   a light source, capable of providing detection light;
   a first light detection portion, capable of detecting the intensity of light;
   a light source modulating portion comprising: a beam splitter capable of splitting the detection light into a first detection light and a second detection light; and a lens capable of focusing the first detection light on the sample, the light source modulating portion being capable of modulating the detection light to a sample and modulating reflected light from the sample to the first light detection portion;
   a second light detection portion, capable of detecting the intensity of light; and
   a reflecting cover comprising: a cone-shaped aperture formed therein for the detection light and the reflected light to pass through; and an elliptic surface with a first focal point located at the sample so that the elliptic surface is capable of modulating the reflected light scattered from the sample to focus on a second focal point of the elliptic surface, the reflecting cover being disposed between the sample and the light source modulating portion, the reflecting cover being capable of introducing the reflected light scattered from the sample to the second light detection portion.

10. The reflectance measuring apparatus as recited in claim 9, wherein the second light detection portion is disposed at the second focal point.

11. The reflectance measuring apparatus as recited in claim 9, wherein the elliptic surface is coated with a reflecting film formed thereon.

12. The reflectance measuring apparatus as recited in claim 9, further comprising a light monitoring portion capable of receiving the second detection light so as to monitor the power intensity of the second detection light.

13. The reflectance measuring apparatus as recited in claim 12, where the light monitoring portion further comprises:

a photo-detector; and a lens, being disposed between the beam splitter and the photo-detector so that the lens is capable of focusing the second detection light on the photo-detector.

14. The reflectance measuring apparatus as recited in claim 9, wherein a lens is disposed between the first light detection portion and the light source modulating portion.

15. The reflectance measuring apparatus as recited in claim 9, wherein the light source is capable of providing a collimated light source.

16. The reflectance measuring apparatus as recited in claim 15, wherein the collimated light source is a laser.

* * * * *